US010317497B2

(12) United States Patent
Neji et al.

(10) Patent No.: US 10,317,497 B2
(45) Date of Patent: Jun. 11, 2019

(54) IMAGING METHOD WITH MULTI-SLICE ACQUISITION

(71) Applicant: Siemens Aktiengesellschaft, Munich (DE)

(72) Inventors: Radhouene Neji, London (GB); David Andrew Porter, Regensburg (DE)

(73) Assignee: Siemens Aktiengesellschaft, Munich (DE)

( * ) Notice: Subject to any disclaimer, the term of this patent is extended or adjusted under 35 U.S.C. 154(b) by 441 days.

(21) Appl. No.: 15/042,183

(22) Filed: Feb. 12, 2016

(65) Prior Publication Data
US 2016/0238685 A1 Aug. 18, 2016

(30) Foreign Application Priority Data

Feb. 13, 2015 (DE) .......................... 10 2015 202 646

(51) Int. Cl.
*G01R 33/36* (2006.01)
*G01R 33/54* (2006.01)
(Continued)

(52) U.S. Cl.
CPC .......... *G01R 33/5616* (2013.01); *A61B 5/055* (2013.01); *G01R 33/36* (2013.01); *G01R 33/3852* (2013.01); *G01R 33/4835* (2013.01); *G01R 33/4836* (2013.01); *G01R 33/543* (2013.01); *G01R 33/5607* (2013.01)

(58) Field of Classification Search
CPC ................ G01R 33/5616; G01R 33/36; G01R 33/3852; G01R 33/4835; G01R 33/4836; G01R 33/543; G01R 33/5607
See application file for complete search history.

(56) References Cited

U.S. PATENT DOCUMENTS

2011/0254548 A1* 10/2011 Setsompop ........ G01R 33/4835
324/309
2012/0056620 A1   3/2012 Feinberg et al.
(Continued)

FOREIGN PATENT DOCUMENTS

WO       2013/171119 A1    11/2013

OTHER PUBLICATIONS

Nagy et al., "Efficient Fat Suppression by Slice-Selection Gradient Reversal in Twice-Refocused Diffusion Encoding," Magnetic Resonance in Medicine, vol. 60, pp. 1256-1260 (2008).
(Continued)

*Primary Examiner* — Rodney A Bonnette
(74) *Attorney, Agent, or Firm* — Schiff Hardin LLP

(57) ABSTRACT

In a method and magnetic resonance (MR) apparatus for acquiring MR signals from an examination object an RF excitation pulse is directed into the examination object while activating magnetic field gradients in two different spatial directions, such that a magnetization in the examination object in the two different spatial directions is limited by the RF excitation pulse and the switching of the magnetic field gradients. The magnetization is excited in one of the two spatial directions, of a slice selection direction, in a number of periodic layers, so MR signals are generated in the multiple periodic slices. The MR signals in the multiple periodic layers are read out using multiple reception coils of the MR scanner.

12 Claims, 2 Drawing Sheets

(51) Int. Cl.
  *G01R 33/56* (2006.01)
  *G01R 33/385* (2006.01)
  *G01R 33/483* (2006.01)
  *G01R 33/561* (2006.01)
  *A61B 5/055* (2006.01)

(56) References Cited

U.S. PATENT DOCUMENTS

2013/0307538 A1 11/2013 Pfeuffer et al.
2015/0084629 A1* 3/2015 Porter .................... G01R 33/54
                                                        324/309
2015/0301143 A1* 10/2015 Banerjee ............ G01R 33/4835
                                                        324/309

OTHER PUBLICATIONS

Setsompop et al., "Blipped-Controlled Aliasing in Parallel Imaging (blipped-CAIPI) for Simultaneous Multi-Slice EPI witth Reduced g-Factor Penalty," Magnetic Resonance in Medicine, vol. 67, pp. 1210-1224, (first published online 2011) (2012).
Haase et al., "1H NMR Chemical Shift Selective (CHESS) Imaging," Phys Med Biol, vol. 30, No. 4, pp. 341-344 (1985).
Saritas et al., "DWI of the Spinal Cord with Reduced FOV Single-Shot EPI," Magnetic Resonance in Medicine, vol. 60, pp. 468-473 (2008).
Hardy et al., "Spatial Localization in Two Dimensions Using NMR Designer Pulses," J. Mag. Res., vol. 82, pp. 647-654 (1989).
Bydder et al., "MR Imaging: Clinical Use of the Inversion Recovery Sequence," Journal of Computer Assisted Tomography, vol. 9, No. 4, pp. 659-675 (1985).
Kaldoudi et al., "A Chemical Shift Selective Inversion Recovery Sequence for Fat-Suppressed MRI: Theory and Experimental Validation," Magnetic Resonance Imaging, vol. 11, pp. 341-355 (1993).

* cited by examiner

US 10,317,497 B2

IMAGING METHOD WITH MULTI-SLICE ACQUISITION

BACKGROUND OF THE INVENTION

Field of the Invention

The present invention relates to a method for acquiring magnetic resonance (MR) signals from an examination object, and an associated MR apparatus.

Description of the Prior Art

For imaging using magnetic resonance installations (MR installations), it is normal practice to direct a two-dimensional excitation pulse into an examination object in order to excite magnetization of nuclear spins in the object. In the case of such an excitation pulse, the RF excitation pulse limits the region in which the magnetization is excited in two spatial directions, which are substantially perpendicular to each other, using two associated magnetic field gradients during the application of the 2D excitation pulse. The two-dimensional excitation pulse is described in Hardy C J et al., "Spatial localization in two dimensions using MR designer pulses", J. Magn. Reson. 1989; 82:647-654. By contrast, in the case of a normal one-dimensional excitation pulse, the magnetization is limited in only one spatial direction by the RF pulse. The two-dimensional excitation pulse is used for imaging in a thin layer in the slice selection direction with a reduced field of view (FOV) in the phase coding direction, with the field of view in the phase decoding direction being reduced relative to the excitation with a one-dimensional excitation pulse. As a result of the reduced field of view, it is possible to improve the image quality by reducing the number of spatial coding steps that are required in the phase coding direction. This reduces the duration of the overall signal acquisition, which in turn reduces the artifacts caused by amplitude or phase changes. The amplitude changes are caused by T2 or T2* relaxation processes and the phase changes are produced by frequency differences due to the chemical shift and due to an inhomogeneity of the polarization field B0.

In the context of these imaging methods with reduced field of view, it is important to reduce unwanted signal components from regions outside the excited volume. Although the two-dimensional excitation works well for proton signals in water molecules, it is nonetheless difficult in many cases to suppress signal components from outside the desired volume of protons in fat. These unwanted signal components are added to the signals from the desired field of view and result in image artifacts.

Fat signals represent a particular problem, because the chemical shift of the protons in fat signals lies approximately 3.5 ppm (parts per million) away from the water protons. This corresponds to the difference in the resonance frequency of 224 Hz at 1.5 Tesla or 447 Hz at 3 Tesla. The two-dimensional excitation pulse usually has a frequency response that results in a non-ideal excitation pattern at a frequency offset which corresponds to the frequency of the fat resonance, and this results in the fat components being incorrectly localized in the desired field of view, even though these fat signal components lie outside the field of view.

Fat signal components are also disruptive in the case of certain measurements such as diffusion-weighted imaging methods, e.g. if the signal reduction of the water signal is greater than that of the fat signal, which increases the relative signal component of the fat.

In addition to the desire to suppress the fat signal outside the field of view, is often desirable to suppress the fat signal inside the field of view or within the region to be examined. This applies to EPI (echoplanar imaging) methods in particular, since the offset caused by the chemical shift produces an incorrect spatial coding between the fat signals and the water signals in the spatially coded image, and EPI methods are particularly sensitive to this.

In "DWI of the spinal cord with reduced FOV single-shot EPI", Magn. Reson. Med. 2008, 60:468-473, Saritas et al. have shown that two-dimensional excitation pulses can be used in such a way as to produce a spatial offset in the slice selection direction between the examination region for the water protons and the examination region for the fat protons. It is then possible to generate an MR image on the basis of the water signal components alone, using a one-dimensional focusing pulse which selectively refocuses the magnetization during the spatial localization of the water protons. This method is effective for the suppression of fat signal components outside and inside the field of view, but this method has the disadvantage that the two-dimensional excitation in the slice selection direction is periodic, meaning that layers are excited periodically at intervals in the slice selection direction. This limits the number of layers that are picked up during a measurement, since the number of layers is limited by the periodicity of the excited slices.

Fat signal components can also be suppressed by further methods as follows:

Fat signals can be suppressed by frequency-selective fat excitation of the fat signal components over the whole examination object. However, this requires a high degree of homogeneity of the polarization field B0 and a homogeneous RF field for exciting the fat signal components. It is often not possible to generate the required homogeneity of the B0 field.

Also known is a so-called STIR method (Short Tau Inversion Recovery), in which a layer-selective inversion pulse is used to invert the magnetization. An inversion time T1 is then selected such that due to the T1 relaxation the magnetization of the fat signal component reaches the zero point with no magnetization along the direction of the polarization field B0. The imaging sequence is then started, whereby in the ideal case no fat signal components are produced. However, the inversion is applied for all regions of the examination object and has the disadvantage that it also reduces the signal-to-noise ratio of the water protons, since it involves a T1-dependent reduction of the signal in the B0 field direction. This technique is also restricted in that the properties of the layer-selective inversion, such as the layer profile and the bandwidth, must be compatible with the other RF pulses for the layer selection, which can mean limitations in the design of the imaging sequence and result in non-optimal fat suppression.

Also known are inversion imaging methods which use selective inversion depending on the chemical shift, wherein the inversion pulse is not used in the slice selection direction here, but as a frequency-selective pulse over the whole examination object. This likewise requires an often unachievable mobility of the polarization field B0.

SUMMARY OF THE INVENTION

An object of the present invention is to at least partially overcome the disadvantages cited above, and in particular to provide a method in which the number of slices to be measured is not limited in the slice selection direction.

According to a first aspect, a method is provided for acquiring MR signals from an examination object by operation of a scanner of an MR installation, wherein an RF excitation pulse is directed into the examination object while switching magnetic field gradients in two different spatial directions, so that an excitation of magnetization in the examination object that deviates from the basic field polarization is limited in the two different spatial directions by the RF excitation pulse and the switching of the magnetic field gradients. The magnetization here is excited in one of the two spatial directions, of a slice selection direction, in a number of periodic (successive) slices. MR signals are then generated in the multiple cyclic slices. The MR signals in the multiple periodic slices are read out using multiple receive coils of the MR scanner. As a result of generation and acquisition of MR signals in the multiple periodic slices, the entirety of the examination region is no longer limited by the periodicity of the slices in the slice selection direction.

The MR signals in the multiple periodic slices are preferably generated by directing an RF refocusing pulse into the examination object, wherein the RF refocusing pulse has a number of frequency bands and refocuses the magnetization in the multiple periodic layers.

By using an RF refocusing pulse that can simultaneously refocus the magnetization in multiple periodic slices, the magnetization having different frequencies in each case, it is possible to acquire raw MR data from multiple slices in the slice selection direction. Overall, this means that the field of view through the periodically excited slices is no longer limited in the slice selection direction.

A readout magnetic field gradient can be switched (activated) during the readout of the MR signals, with a coding magnetic field gradient being switched in the slice selection direction during the readout of the MR signals in such a way that the MR signals which are acquired in the multiple periodic layers have a different phase pattern. For example, the slice selection magnetic field gradient that is switched during the readout of the MR signals may be switched in accordance with a CAIPIRINHA method, preferably a blipped CAIPIRINHA method, in which the magnetization in the slice selection direction is used by coding magnetic field gradients of short duration and low amplitude, called blips, wherein adjacent blips have different polarity. The CAIPIRINHA method and the blipped CAIPIRINHA method are described in greater detail in US 2011/0254548 A1.

The different phase pattern can also be achieved by modulating the phase of the multiband RF pulse. When using multiple RF excitation pulses, the phase of the various RF pulses may be so selected as to differ.

The coding magnetic field gradient can therefore be switched by multiple magnetic field gradient pulses in the slice selection direction, wherein adjacent magnetic field gradient pulses have opposite polarity. Therefore, the phase pattern of the MR signals that are acquired can be controlled in the slice selection direction by these coding gradients. As a result of the phase shift, image points from different layers experience a greater spatial shift, thereby aiding the readout of the MR signals in the different slices.

During the signal readout, readout magnetic field gradients may be used in accordance with an echoplanar method. However, the invention is not limited to echoplanar methods, and it is also possible to use simple spin echo or gradient echoes with separate excitation for each line of raw data, or multi-spin echo sequences in which multiple spin echoes per readout cycle are picked up. Use with segmented EPI sequences is also conceivable.

It is also possible for one of the magnetic field gradients activated during the RF excitation pulse to be switched in the slice selection direction by multiple magnetic field gradient pulses in the slice selection direction, wherein adjacent magnetic field gradient pulses have identical polarity. As a result of these gradient pulses in the slice selection direction, the blips in the slice selection direction, and the relatively long time interval between the individual blips, the periodicity of the two-dimensional excitation pulse or the periodicity of the excited slices in the slice selection direction is produced.

Moreover, a first magnetic field gradient corresponding to one of the magnetic field gradients in the different spatial directions can be activated in the slice selection direction during the application of the RF excitation pulse, with a second magnetic field gradient being activated in the slice selection direction during the application of the RF refocusing pulse. These first and second magnetic field gradients preferably have opposite polarity.

It is also possible to use the method described above for the purpose of generating diffusion-weighted MR images, wherein diffusion-weighted magnetic field gradients are also switched in different spatial directions, or at least one spatial direction, between the RF excitation pulse and the signal readout.

The RF refocusing pulse is preferably designed to be a single RF refocusing pulse having different frequency components, and not generated by two temporally separate refocusing pulses having different frequencies.

The invention further concerns a magnetic resonance apparatus designed to acquire the MR signals as described above, having scanner with an RF unit for applying the RF excitation pulse and the RF refocusing pulse as described above, an image sequence controller that controls the RF pulses and magnetic field gradients as described above, and a signal readout unit which has a number of receive coils and that reads out the MR signals in the multiple periodic layers using the multiple receive coils.

DESCRIPTION OF THE PREFERRED EMBODIMENTS

Figure 1:
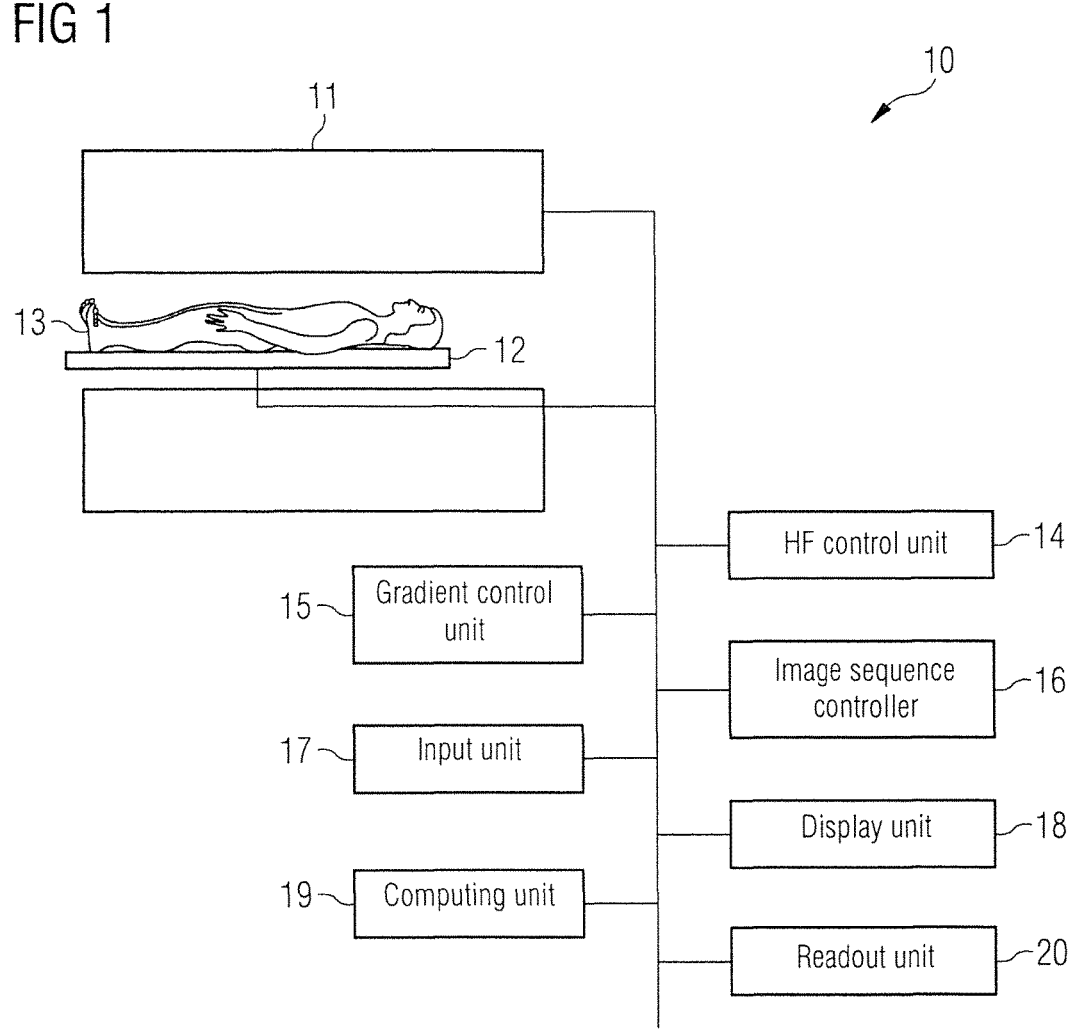
FIG. 1 schematically shows an MR apparatus with which MR signals can be read out according to the invention in multiple periodic excited slices.

FIG. 1 schematically shows an MR apparatus with which according to the invention, MR images are generated from multiple periodically excited slices. The MR apparatus 10 has a scanner with a magnet 11 for generating a polarization field B0. An examined person 13 arranged on a bed 12 is situated in the magnet 11, resulting in a magnetization in the direction of the polarization field B0. Using magnetic field gradient coils (not shown), temporally varying magnetic field gradients are activated for spatial coding of the magnetization. The MR installation 10 also has transmit and receive RF coils (not shown) by which RF pulses can be directed into the examined person 13, in order to deflect the magnetization, and by which signals emitted by the nuclear spins resulting transverse magnetization can be detected. An RF control processor 14 is provided for generating the RF pulses that are directed into the examined person. As explained below in further detail, the RF control processor is designed to direct a two-dimensional excitation pulse into the examined person, such that the magnetization is limited in two discrete spatial directions by the RF pulse. A gradient control processor 15, which controls the switching (activation) of the magnetic field gradients, is also provided for this purpose. Depending on the selected imaging sequence, an image sequence controller 16 determines the timing sequence in which the RF pulses and the magnetic field gradients are used, and therefore also controls inter alia, the gradient control processor 15 and the RF control processor 14.

An input interface 17 allows an operator of the MR apparatus 10 to operate the MR apparatus 10, select imaging sequences, specify imaging planes, etc.

The generated MR images can be displayed on a display monitor 18. A computer 19 calculates the MR images from the detected signals. A readout unit 20 is responsible for controlling the signal readout via the receive coils (not shown). In particular, the MR installation has multiple reception coils for the purpose of simultaneously receiving MR signals via the respective reception coils.

The manner in which the magnetization can be spatially coded by the sequence of magnetic field gradients and RF pulses, and in which the MR images can be generated after reading out the MR signals, are known to those skilled in the art and thus need not be explained in detail herein. Moreover, the MR apparatus 10 shown in FIG. 1 can have further functional units, which are not illustrated. Similarly, the functional units do not have to be implemented individually as illustrated in FIG. 1. Individual functional units or a number of the functional units shown in FIG. 1 may also be implemented in a single unit. Furthermore, an implementation is possible in hardware, in software or in a combination of both hardware and software.

Figure 2:
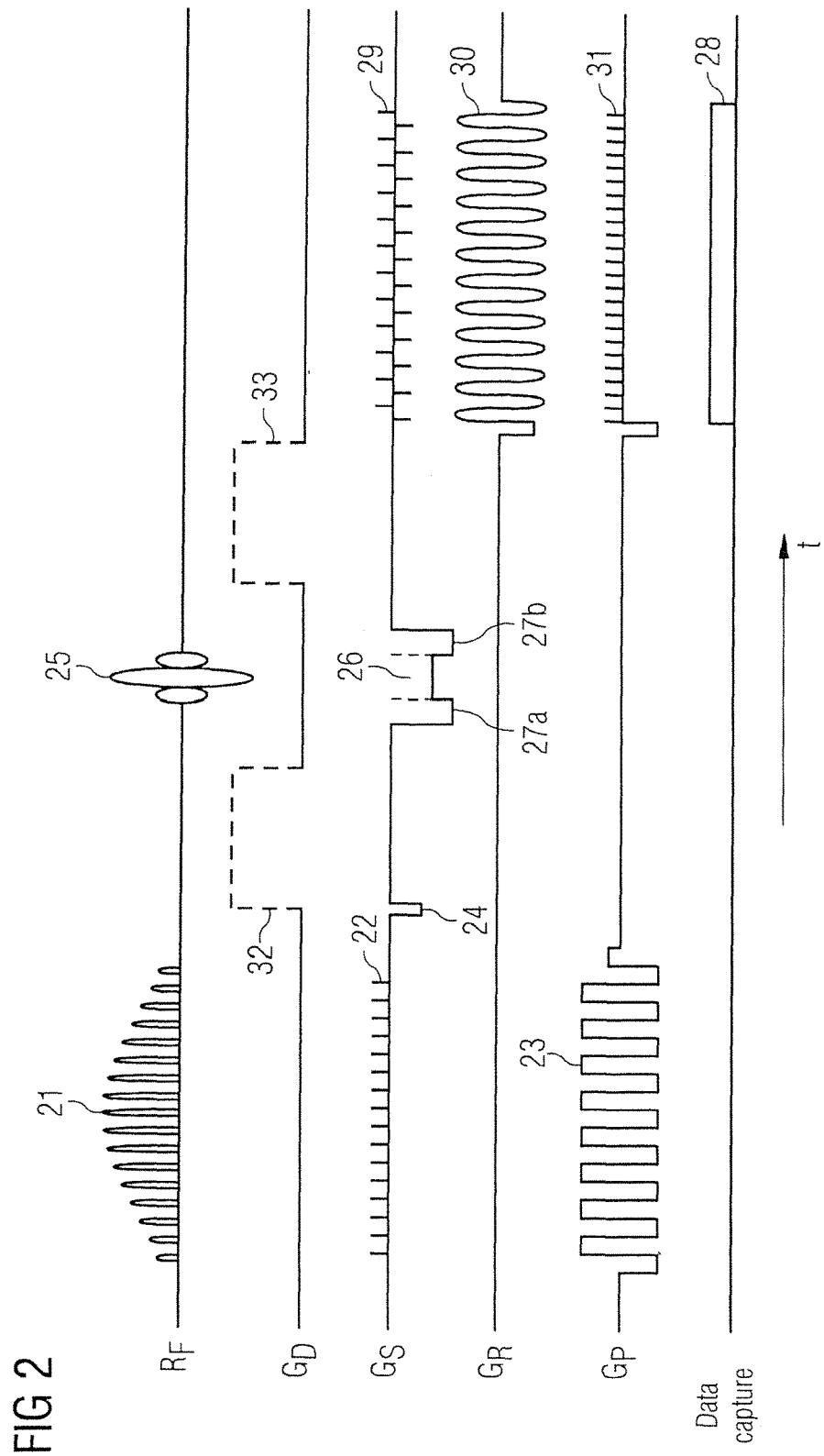
FIG. 2 shows an imaging sequence by which multiple periodic slices can be acquired using a method according to the invention.

FIG. 2 shows the inventive imaging sequence, which has no restrictions as to the number of slices from which MR data are acquired in the slice selection direction. At the top of FIG. 2, the temporal course is shown for the RF pulses that are applied. The two-dimensional excitation can be achieved by the illustrated temporal course of an RF pulse 21, which is a 90° excitation pulse in the embodiment shown. At the same time, a magnetic field gradient 22 as shown is switched in the slice selection direction during the signal excitation, specifically using short magnetic field gradient pulses in the slice selection direction during the RF radiation. Furthermore, the magnetic field gradient 23 is switched in the phase coding direction. As a result of the combination of the magnetic field gradients 22, 23 and the RF excitation pulse 21, nuclear spins in a slice are excited which is defined and limited in two orthogonal directions by the RF pulse excitation and the magnetic field gradients. This means that only part of the examination object, rather than the whole examination object, is usually excited in the phase coding direction, and it is therefore possible, e.g. in the case of a sagittal section through an examined person, to excite not the whole examined person, but only the region around the spinal column. The gradient 24 is then switched in the slice selection direction, in order overall to set the gradient moment resulting from the gradients 22 and 24 to zero. A multi-slice RF refocusing pulse 25 is also directed into the examination object. As a result of the application as shown in FIG. 2 of the RF excitation pulse 21 and the gradients in the slice selection direction, the magnetization is periodically excited in a number of slices in the examination object, e.g. the examined person 13 from FIG. 1, meaning that the magnetization in the slice selection direction is excited at periodic intervals by the RF excitation pulse 21. The refocusing pulse 25 is preferably a 180° pulse. This refocusing pulse is so designed as to have a number of spectral frequency bands, these being selected such that the many periodic slices generated by the excitation pulse 21 are affected by the refocusing pulse. Therefore, in the case of a 180° refocusing pulse, the magnetization generates a spin echo in the at least two excited slices, these being parallel to each other in the slice selection direction. During this multi-slice refocusing pulse 25, the magnetic field gradient 26 is switched in the slice selection direction. In the example shown, this magnetic field gradient is framed by further dephasing gradients 27a and 27b, which destroy (spoil) the signal from any unwanted signal components such as the signal of an FID (Free Induction Decay), such that only the spin echo signal components from those layers which are excited in parallel contribute to the signal. The MR signals are then acquired during a time period 28. During this time period, a magnetic field gradient 29 (also referred to as a coding magnetic field gradient) having short magnetic field gradient pulses, so-called blips having reversed polarity of adjacent magnetic field gradients, is switched in the slice selection direction as shown.

By virtue of these additional magnetic field gradients in the slice selection direction, the signal phase of the MR signals is modulated or coded such that the MR signals in the individual parallel slices have different phase values. Therefore the individual layer-specific signals can be separated from each other more effectively. This produces a phase pattern in the ky direction, which varies from slice to slice. This slice-dependent phase pattern in turn generates an image shift which varies from slice to slice in the MR image.

A signal readout gradient 30 is also switched during the signal readout, this signal readout gradient being switched in a manner that is known from echoplanar imaging. In addition, as is known from EPI imaging, a gradient switching 31 is switched in the phase coding direction with a negative pregradient and short positive blips in the phase coding direction. It is likewise possible to use a positive pregradient and negative blips. Also illustrated schematically are diffusion gradients 32 and 33, which can be used before or after the refocusing pulse. These diffusion gradients 32 and 33 can be switched in one of the three spatial directions for the purpose of selection, phase coding or readout direction, in two of the three or in all three spatial directions for the purpose of generating diffusion-weighted MR images, which can then be used to calculate a diffusion tensor in a known manner.

It can be seen in FIG. 2 that the polarity of the layer selection gradient during the RF excitation pulse 21 is opposite to the polarity of the layer selection gradient 26 during the refocusing pulse 25. This allows better separation between the fat regions which are excited by the 2D excitation pulse 21 and by the refocusing pulse 25. The unwanted signal component of the fat can therefore be reduced overall.

In the case of the method described in FIG. 2, the signal readout is performed according to the echoplanar method, wherein the spin echo generated in the various layers is picked up during this signal readout, and wherein gradient echoes are also produced by the signal readout gradient 30 in readout direction. However, the method is not limited to so-called single-shot EPI methods, in which the whole raw data space is picked up after switching the pulses 21, 25 once. It is also possible to use segmented EPI methods, in which only certain segments and not the whole raw data space are read out following an RF excitation pulse 21. Moreover, it is possible to pick up only gradient echo signals or simple spin echo signals, with separate excitation for each line of the raw data space. It is also possible to use quick spin echo sequences, which use a number of refocusing pulses such as the refocusing pulses 25, when reading out a number of raw data lines following excitation.

In summary, the imaging method described in connection with FIG. 2 offers a procedure for acquiring, with effective suppression of unwanted signal components, a number of slices in the slice selection direction using a single pass of the imaging sequence illustrated in FIG. 2. It is thereby possible generally to increase the number of slices that are to be picked up in the slice selection direction.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring magnetic resonance (MR) signals from an examination object, said method comprising:
   while an examination object is situated in an MR scanner, providing control signals from a computer in order to operate the MR scanner so as to radiate a radio-frequency (RF) excitation pulse from an RF radiator of said MR scanner into the examination object while activating magnetic field gradients from said gradient coils of said MR scanner respectively in two different spatial directions, with a first of said magnetic field gradients being activated in one of said two different spatial directions with a first polarity and a second of said magnetic field gradients being activated in another of said two different spatial directions with a second polarity that is opposite to said first polarity, and thereby producing a magnetization of nuclear spins in the examination object in said two different spatial directions, limited by said RF excitation pulse and the activated magnetic field gradients, said magnetization of said nuclear spins being produced in one of said two spatial directions, as a slice selection direction, in a plurality of periodic slices and said magnetization causing MR signals to be emitted by said nuclear spins in said plurality of periodic slices;
   with said control signals from said computer, operating said MR scanner to read out said MR signals in said plurality of periodic layers using a plurality of reception coils of the MR scanner; and
   making the MR signals available in electronic form from the computer as a data file for further processing thereof.

2. A method as claimed in claim 1 comprising generating said MR signals in said plurality of periodic slices by radiating an RF refocusing pulse from said RF radiator in said MR scanner, said RP refocusing pulse having a plurality of refocusing bands and refocusing the magnetization in the plurality of periodic layers.

3. A method as claimed in claim 1 comprising operating said gradient coils of said MR scanner to read out said MR signals by activating a readout magnetic field gradient and by activating a spatially coding magnetic field gradient in said slice selection direction during readout of said MR signals, that gives the MR signals a different phase pattern in the plurality of periodic slices.

4. A method as claimed in claim 3 comprising activating said spatially coding magnetic field as a plurality of magnetic field gradient pulses in said slice selection direction, with adjacent magnetic field pulses in said plurality of magnetic field pulses having opposite polarity.

5. A method as claimed in claim 1 comprising activating one of the magnetic field gradients during said RF excitation pulse in the slice selection direction as a plurality of magnetic field gradient pulses in said slice selection direction, with adjacent magnetic field gradient pulses in said plurality of magnetic field gradient pulses having identical polarity.

6. A method as claimed in claim 1 comprising:
   generating said MR signals in said plurality of periodic slices by radiating an RF refocusing pulse from said RF radiator of said MR scanner, said RF refocusing pulse having a plurality of refocusing bands and refocusing the magnetization in the plurality of periodic layers;
   activating said first magnetic field gradient in said slice selection direction during radiation of said RF excitation pulse; and
   activating said second magnetic field gradient during radiation of said RF refocusing pulse.

7. A method as claimed in claim 1 comprising operating said MR scanner to activate diffusion-weighted magnetic field gradients in at least one of said spatial directions, between said RF excitation pulse and readout of said MR signals, and post-processing said MR signals in said data file to reconstruct a diffusion-weighted image of said examination object.

8. A method as claimed in claim 1 comprising generating said MR signals in said plurality of periodic slices by radiating a single RF refocusing pulse from said RF radiator of said MR scanner, said RF refocusing pulse having a plurality of refocusing bands and refocusing the magnetization in the plurality of periodic layers.

9. A method as claimed in claim 1 comprising:
   with said control signals, operating said MR scanner with an echo planar imaging sequence that includes radiating said RF excitation pulse and activating said magnetic field gradients; and
   reading out said MR signals by activating a readout gradient during echoes that occur in said echo planar imaging sequence.

10. A method as claimed in claim 1 comprising reconstructing image data from said MR signals and displaying the image data, as an MR image of the examination object, at a display screen.

11. A magnetic resonance (MR) apparatus comprising:
    an MR scanner comprising a radio-frequency (RF) radiator, a plurality of RF reception coils, and a gradient coil arrangement;
    an RF controller configured to operate said RF radiator to radiate at least one RF excitation pulse into an examination object situated in said MR scanner;
    a gradient controller configured to operate said gradient coil arrangement to activate magnetic field gradients respectively in two different spatial directions, while said examination object is situated in an MR scanner and while radiating said RF excitation pulse, with a first of said magnetic field gradients being activated in one of said two different spatial directions with a first polarity and a second of said magnetic field gradients being activated in another of said two different spatial directions with a second polarity that is opposite to said first polarity, and thereby producing a magnetization of nuclear spins in the examination object in said two different spatial directions, limited by said RF excitation pulse and the activated magnetic field gradients, said magnetization of said nuclear spins being produced in one of said two spatial directions, as a slice selection direction, in a plurality of periodic slices, and said magnetization causing MR signals to be emitted from said nuclear spins in said plurality of periodic slices;

a control computer configured to operate said MR scanner to read out said MR signals in said plurality of periodic layers using said plurality of reception coils of the MR scanner; and said control computer being configured to make the MR signals available in electronic form as a data file for further processing thereof.

12. An MR apparatus as claimed in claim 11 comprising a reconstruction computer configured to reconstruct image data from said MR signals, and a display screen in communication with said reconstruction computer at which said image data are displayed as an MR image of the examination object.

* * * * *